US00PP37514P2

(12) United States Plant Patent
Nannes

(10) Patent No.: US PP37,514 P2
(45) Date of Patent: Jul. 7, 2026

(54) ***NEMATANTHUS* PLANT NAMED 'BINL-110919'**

(50) Latin Name: *Nematanthus gregarius*
Varietal Denomination: BINL-110919

(71) Applicant: Botanical Innovation B.V., Wageningen (NL)

(72) Inventor: Jacobus A. M. Nannes, Nairobi (KE)

(73) Assignee: Botanical Innovation B.V. (NL)

( * ) Notice: Subject to any disclaimer, the term of this patent is extended or adjusted under 35 U.S.C. 154(b) by 0 days.

(21) Appl. No.: 19/345,001

(22) Filed: Sep. 30, 2025

(51) Int. Cl.
*A01H 5/12* (2018.01)
*A01H 6/44* (2018.01)

(52) U.S. Cl.
USPC ..... Plt./373

(58) Field of Classification Search
USPC ..... Plt./373, 263.1
CPC ..... A01H 5/12; A01H 5/00; A01H 6/44
See application file for complete search history.

(56) References Cited

PUBLICATIONS

Fialkin *Nematanthus gregarius* Golden West retrieved on Jan. 27, 2026 at https://www.fialkin.ru/katalogi_rasteniy/drugie_gesnerivye/nematanthus_gregarius_golden_west.html, 2 pp. (Year: 2026).*

* cited by examiner

*Primary Examiner* — June Hwu

(57) ABSTRACT

A new and distinct cultivar of *Nematanthus* plant named 'BINL-110919' is disclosed, characterized by distinctly variegated leaves with a unique combination of colors. Variegated leaves have an irregular light green center, fading out into an irregular yellow outer leaf. The young leaves have a very thin/narrow dark red leaf-rim/edge. The new variety is a *Nematanthus*, typically produced as an ornamental plant.

1 Drawing Sheet

Latin name of the genus and species: *Nematanthus gregarius*.

Variety denomination: 'BINL-110919'.

BACKGROUND OF THE INVENTION

The new cultivar is a product of a naturally-occurring branch mutation. The parent cultivar is the unpatented *Nematanthus gregarius*, the species itself. The new cultivar was found and selected by the inventor in September 2022 at a nursery in Nairobi, Kenya.

Asexual reproduction of the new cultivar 'BINL-110919' was first performed in Nairobi, Kenya in May 2023, by top cuttings. 'BINL-110919' has since produced several generations and has shown that the unique features of this cultivar are stable and reproduced true to type.

SUMMARY OF THE INVENTION

The cultivar 'BINL-110919' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-110919'. These characteristics in combination distinguish 'BINL-110919' as a new and distinct *Nematanthus* cultivar:

1. Distinctly variegated leaves with a unique combination of colors. Variegated leaves have an irregular light green center, fading out into an irregular yellow outer leaf. The young leaves have a very thin/narrow dark red leaf-rim/edge.

PARENTAL COMPARISON

Plants of the new cultivar 'BINL-110919' are similar to the parent in most horticultural characteristics. However, plants of the new variety differ in the following:

1. Leaves of the new variety are variegated with an irregular light green center, fading out into an irregular yellow outer leaf; young leaves have a very thin/narrow dark red leaf-rim/edge. Leaves of the parent are non-variegated with a glossy, fully dark green color on the leaf-upperside. The leaf-downside is light green.

COMMERCIAL COMPARISONS

'BINL-110919' can be compared to the commercial variety *Nematanthus gregarius* 'Miami', unpatented. The two varieties are similar in most horticultural characteristics; however, the new variety differs in the following:

1. Leaves of the new variety are variegated with an irregular light green center, fading out into an irregular yellow outer leaf; young leaves have a very thin/narrow dark red leaf-rim/edge. Leaves of this comparator are non-variegated, having a glossy, fully green color on the leaf-upperside. The leaf-downside is also fully green.

'BINL-110919' can be compared to the unpatented commercial variety *Nematanthus gregarius*, 'Variegata'. The two varieties are similar in most horticultural characteristics; however, the new variety differs in the following:

1. Leaves of the new variety are variegated with an irregular light green center, fading out into an irregular yellow outer leaf; young leaves have a very thin/narrow dark red leaf-rim/edge. Leaves of this comparator are non-variegated, having a glossy, irregular dark green leaf-rim and an irregular yellow-white leaf-center.

BRIEF DESCRIPTION OF THE PHOTOGRAPH

The accompanying photograph illustrates in full color a close-up view of the foliage on a typical plant of 'BINL-110919' grown in a greenhouse in Nairobi, Kenya. This plant is approximately 10 weeks old, shown in a 12 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, sixth edition, except where general terms of ordinary dictionary significance are used. The following observations and measurements describe 'BINL-110919' plants in a glass greenhouse in Nairobi, Kenya. Temperatures ranged from 20° C. to 28° C. during the day, and 12° C. to 20° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Nematanthus gregarius* 'BINL-110919'.

PROPAGATION

Time to initiate roots: 7 days in summer; 14 days in winter at 20° C.

Time to produce rooted cutting: 30 days in summer; 45 days in winter at 20° C.

Root description: Thin, herbaceous, moderately dense and freely-branching. White in color, not accurately measured with The R.H.S. Chart.

Propagation method: Top cuttings.

PLANT

Plant type: Perennial potted plant.

Plant shape: Obovate.

Age of the plant described: 14 weeks.

Growth habit: Main stems, with lateral branches present.

Container size: 7 cm pots and larger.

Height: Average 9.2 cm; no flowering observed.

Plant spread: Average 15.2 cm.

Growth rate: Moderate.

Vigor: Moderate.

Branching characteristics: Main stems grow from base, with lateral branches. No pinching required.

Number of primary stems per plant: Average 3.

Number of secondary stems per plant: Average 5.

Main branches:

- *Length*.—Average 7.3 cm.
- *Diameter*.—Average 2.0 mm.
- *Internode length*.—Average 3.8 cm.
- *Appearance and shape*.—Circular.
- *Luster*.—Glossy.
- *Aspect/angle from vertical*.—Average 35°.
- *Strength*.—Moderately strong.
- *Color*.—Developing: RHS Greyed-Purple N186C. Mature: RHS Yellow-Green 146A. At internodes: RHS Yellow-Green 144A, two small glands on either side Greyed- Green 193D.
- *Pubescence*.—Thin whitish hairs, 1.0 mm and shorter, impossible to measure accurately with RHS-CC due to sparseness and size.

FOLIAGE

Leaf:

- *Arrangement*.—Opposite, single.
- *Quantity*.—Average 6.
- *Average length*.—3.1 cm.
- *Average width*.—1.7 cm.
- *Whole leaf shape*.—Elliptic.
- *Whole leaf aspect*.—Concave.
- *Apex*.—Acute.
- *Base*.—Attenuate.
- *Margin*.—Slightly revolute.
- *Texture of top surface*.—Glabrous, smooth, moderately leathery.
- *Texture of bottom surface*.—Glabrous, smooth, moderately leathery.
- *Pubescence*.—None.
- *Rugosity*.—Both sides non-rugose.
- *Luster*.—Upper side: Moderately glossy. Under side: Matte.
- *Color*.—Young foliage upper side: Irregularly center blotched RHS Green 137B and Yellow-Green 143C and 144A, irregularly, broadly margined Yellow-Green N144A, thinly edged Greyed-Purple 183C. Young foliage under side: RHS Greyed-Green 194C, irregularly, broadly margined Yellow-Green 150D, thinly edged Greyed-Purple 185A. Mature foliage upper side: Irregularly center blotched Yellow-Green 146A and 146B, irregularly, broadly margined Yellow-Green 144A, occasionally thinly edged Greyed-Purple; a blend of 187B and 178B. Mature foliage under side: Irregularly blotched Yellow-Green 146A and 146B, irregularly, broadly margined Yellow-Green 144B, occasionally thinly edged Greyed-Purple; a blend of 187B and 178B.
- *Venation*.—Pattern: Pinnate. Color, upper side: Main vein not visible. Color, under side: Main vein RHS Yellow-Green 146A.

Petioles:

- *Length*.—Average 0.5 cm.
- *Diameter*.—U-shaped, average horizontal and vertical diameter 0.15 cm.
- *Texture*.—Glabrous, smooth, moderately leathery.
- *Luster*.—Both sides matte.
- *Strength*.—Moderately strong.
- *Color, upper side*.—RHS Yellow-Green 144B.
- *Color, under side*.—RHS Yellow-Green N144A.

FLOWER

Flowering not observed to date.

REPRODUCTIVE ORGANS

Not observed to date.

OTHER CHARACTERISTICS

Seeds and fruits: Not observed to date.

Temperature tolerance: Unknown, at least tolerant to temperatures from 5° C. to 40° C. USDA zone 11 to 13.

Tolerance to wind and rain: Moderate to high tolerance to rain; moderate tolerance to wind.

Disease/pest resistance: Neither resistance nor susceptibility to the normal diseases and pests of *Nematanthus* observed.

What is claimed is:

1. A new and distinct cultivar of *Nematanthus* plant named 'BINL-110919' as herein illustrated and described.

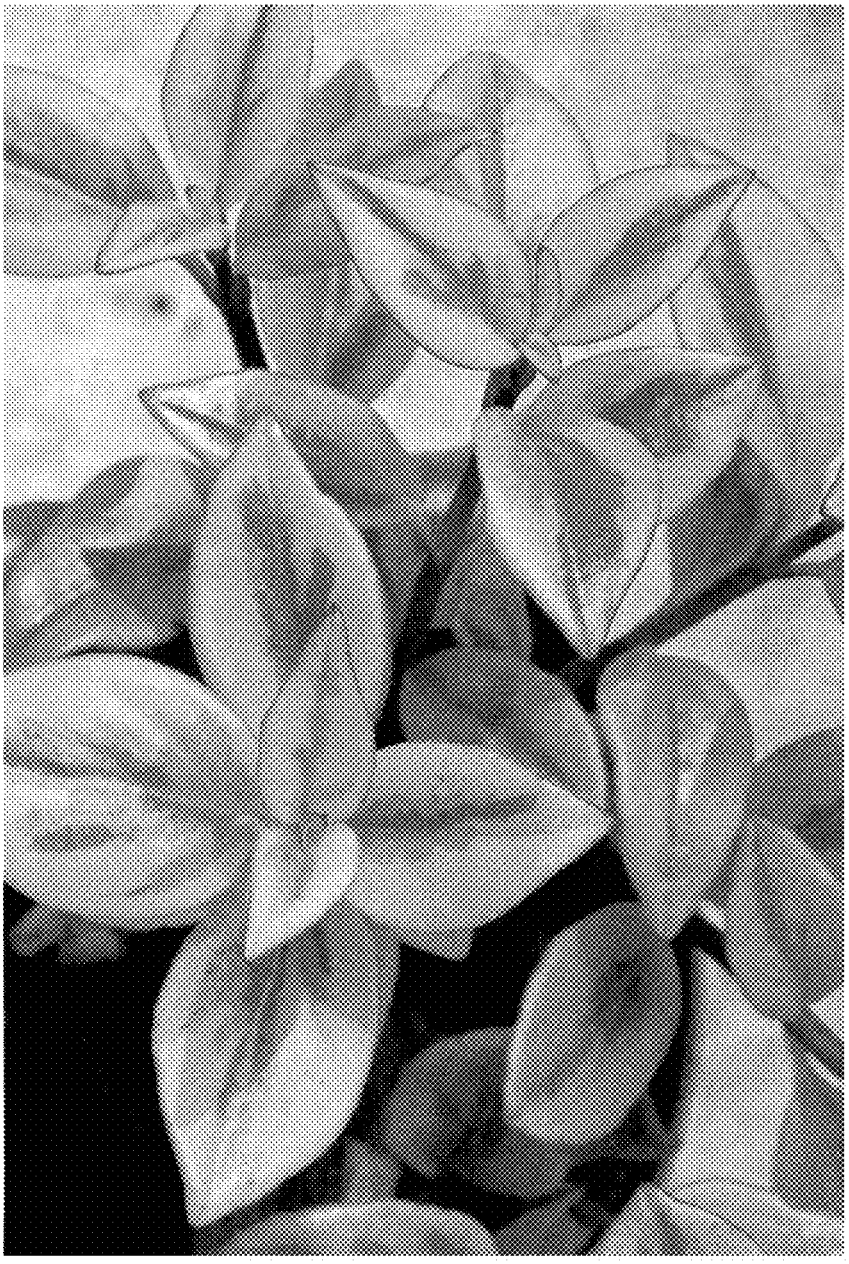

* * * * *